US005871549A

United States Patent [19]

Jayashankar et al.

[11] Patent Number: 5,871,549

[45] Date of Patent: *Feb. 16, 1999

[54] FEMORAL STEM WITH REDUCED COEFFICIENT OF FRICTION WITH RESPECT TO BONE CEMENT

[75] Inventors: C. M. Jayashankar, Raynham; Frank D. Matthews, III, Walpole; Jorge A. Ochoa, Norton, all of Mass.

[73] Assignee: Johnson & Johnson Professional, Inc., Raynham, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 764,156

[22] Filed: Dec. 12, 1996

[51] Int. Cl.$^{6}$ .......... A61F 2/32

[52] U.S. Cl. .......... 623/22; 623/16; 623/23

[58] Field of Search .......... 623/23, 22, 16, 623/18

[56] References Cited

U.S. PATENT DOCUMENTS

| | | | |
|---|---|---|---|
| 4,619,659 | 10/1986 | Witzel | 623/23 |
| 4,770,661 | 9/1988 | Oh | 623/23 |
| 4,888,023 | 12/1989 | Averill et al. | 623/22 |
| 5,047,054 | 9/1991 | Vijayan et al. | 623/16 |
| 5,061,286 | 10/1991 | Lyle | 623/16 |
| 5,308,180 | 5/1994 | Pournoor et al. | 604/3 |
| 5,370,694 | 12/1994 | Davidson | 623/22 |
| 5,380,547 | 1/1995 | Higgins | 623/16 |
| 5,447,966 | 9/1995 | Hermes et al. | 523/113 |
| 5,458,651 | 10/1995 | Lawes | 623/18 |
| 5,480,449 | 1/1996 | Hamilton et al. | 623/66 |
| 5,578,046 | 11/1996 | Liv et al. | 606/76 |
| 5,593,452 | 1/1997 | Higham et al. | 623/23 |
| 5,593,719 | 1/1997 | Dearnaley et al. | 427/2.26 |

OTHER PUBLICATIONS pp. 679–685, of *The Biomedical Engineering Handbook*, (Joseph D. Bronzino, ed., CRC Press and IEEE Press 1995).

*Primary Examiner*—Michael J. Milano
*Assistant Examiner*—Tram A. Nguyen
*Attorney, Agent, or Firm*—Nutter, McClennen & Fish, LLP

[57] ABSTRACT

An orthopedic device is provided having a femoral stem with a proximal end, a distal end, and an intermediate portion extending between the proximal end and the distal end. The intermediate portion tapers from a first cross-sectional geometry near the proximal end to a second cross-sectional geometry near the distal end. A surface region of the femoral stem has a coefficient of friction less than 0.3 with respect to a bone cement. The surface region can include a treated metal region integral with the stem, or a friction reducing coating or sheath that coats or covers a portion of the stem. A collar can be provided near the proximal end of the stem that has a greater diameter than the first diameter of the stem.

3 Claims, 2 Drawing Sheets

22
24
18
12
26
20
10
16
31
14

FEMORAL STEM WITH REDUCED COEFFICIENT OF FRICTION WITH RESPECT TO BONE CEMENT

CROSS-REFERENCE TO RELATED APPLICATIONS

Not Applicable

STATEMENT REGARDING FEDERALLY SPONSORED RESEARCH

Not Applicable

FIELD OF THE INVENTION

The present invention relates to prosthetic implants, and more particularly to a femoral stem configured to readily subside in bone cement.

BACKGROUND OF THE INVENTION

A hip stem is a prosthetic medical implant that replaces the upper portion of a femur that has been resectioned during an arthroplasty procedure. The hip stem includes an elongate portion and a rounded head. The elongate portion is insertable into the medullary canal of the resectioned femur, whereas the rounded head extends from the femur for mating with an acetabular cup that is securable to a hip socket of the pelvis. Together, the hip stem and acetabular cup comprise a prosthetic hip joint.

During an arthroplasty procedure bone cement such as polymethymethacrylate (PMMA) can be deposited into the medullary canal of the femur and the elongate portion of the hip stem is inserted into, and enveloped by, the mass of bone cement. Rough or textured portions of the hip stem bond securely with the bone cement to provide a first interface, and the cement infuses into and bonds with the bone at a second interface. Thus, the hip stem is rigidly secured in place within the femur. However, it has been discovered that even if the femoral stem is flexible, repeated loading and unloading of the prosthetic hip joint during physical activity can cause the bone cement to fatigue and fail.

Uncontrolled breakdown or failure of the bone cement has undesirable consequences, such as free particle generation that can lead to osteolysis or "cement disease" of host bone tissue. Additionally, loose bone cement particles can migrate from the medullary canal to articulating surfaces and act as third body wear generators. This can cause excessive wear of the femoral head and/or a metallic or polymeric counterface within the acetabular cup. With respect to polymeric counterfaces, cement particulate can become embedded in the polymer surface and act as a second body wear surface against the metallic articulating surface of the femoral head.

As the cement breaks down, the hip stem increasingly loosens. And as the hip stem loosens, the bonds between the bone and the cement, and the stem and the cement weaken. The breakdown of these bonds allows the stem to subside or sink into the medullary canal, thereby shortening the leg. As the leg becomes shorter, an undesirable change in patient gait can develop which can continue to deteriorate as the stem subsides. Eventually, the gait deteriorates to such a degree that surgical revision (replacement) of the stem is indicated. Avoidance of the above-described sequence of events would be highly desirable.

SUMMARY OF THE INVENTION

The present invention overcomes the disadvantages inherent with the use of cement in arthroplasty procedures by providing a femoral stem with a configuration that enables a unique stem/cement interface. More particularly, the present invention provides a femoral stem having a shape and surface properties that virtually eliminate stem and cement bonding and which encourage femoral stem subsidence to a limited extent.

In an exemplary embodiment, an orthopedic device includes a femoral stem with a proximal end, a distal end, and an intermediate portion extending between the proximal end and the distal end. The intermediate portion tapers from a first cross-sectional geometry near the proximal end to a second cross-sectional geometry near the distal end. A surface region of the femoral stem has a coefficient of friction with bone cement of less than 0.3.

The surface region can include a region integral with the stem having metal treated to render it very lubricous or slippery. Alternatively, a friction reducing coating or sheath can be provided to coat or cover at least a portion of the stem. The coating or cover can include dispersed particles, a fluid, or a substantially solid, discrete layer of low viscosity material.

In addition to the low friction surface, a collar can be provided on the stem to limit the insertion depth of the stem into the medullary canal.

BRIEF DESCRIPTION OF THE DRAWINGS

A more complete understanding of the present invention and the attendant advantages and features thereof will be more readily understood by reference to the following detailed description when it is considered in conjunction with the accompanying drawings wherein.

DETAILED DESCRIPTION OF THE INVENTION

Figure 1:
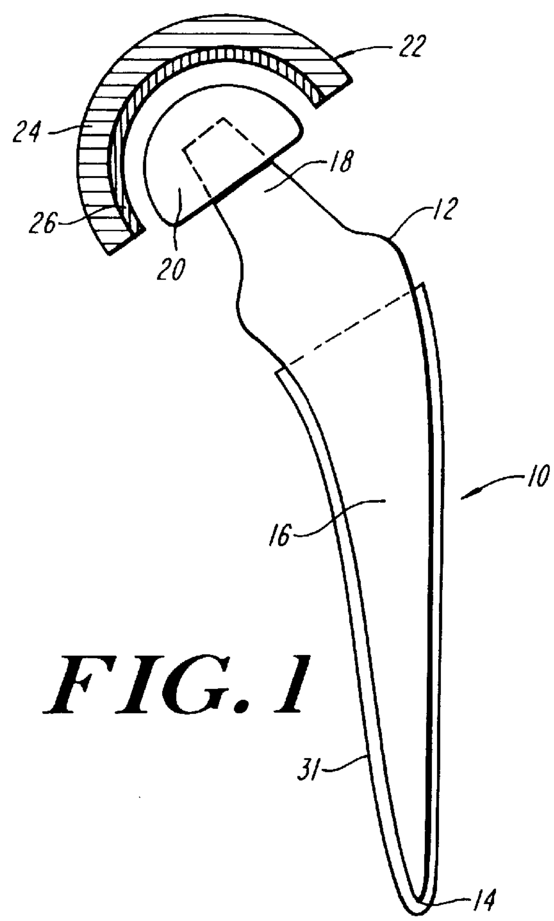
FIG. 1 is perspective view of a femoral stem in accordance with the present invention.

FIG. 1 illustrates an orthopedic device, and more particularly a hip prosthesis, that is configured for an arthroplasty procedure that calls for use of a bone cement. Although the discussion which follows is focused upon the specific features of a hip prosthesis, the inventive features of the invention are equally suitable for and applicable to other prosthetic devices that are insertable into a bone cavity, such as a tibial component.

Figure 7:
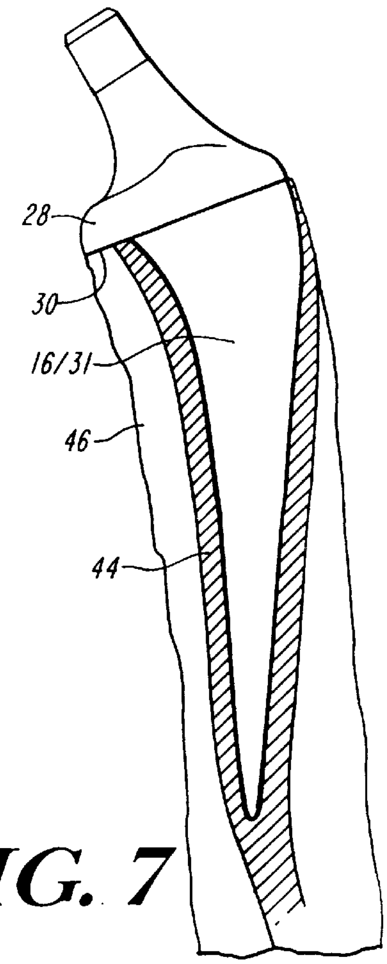
FIG. 7 illustrates an embodiment of the femoral stem positioned within the medullary canal of a femur.

The hip prosthesis includes a first portion 10 adapted for introduction into a medullary canal (illustrated in FIG. 7). The first portion 10 includes a stem having a proximal end 12, a distal end 14, and an intermediate portion 16 extending between the proximal end and the distal end. A second portion 18 or neck, contiguous with the first portion 10, is adapted to engage a second prosthetic component that is external to the medullary canal. The second prosthetic component can be a head 20 that is securable to the second portion 18. However, if the head 20 is integral with the stem, thereby constituting the second portion 18, the second prosthetic component can be an acetabular cup 22 that can include a metal shell 24 with a plastic or polymer liner 26, as is known in the art. The liner 24 includes a hemispherical surface adapted to engage a complimentary spherical surface of the head 20 in a manner that permits smooth movement and rotation of the head within the acetabular cup 22.

The intermediate portion 16 of the first portion 10 tapers from the proximal end to the distal end so that the distal end of the stem is smaller than the proximal end of the stem. The particular angle of taper is determined in part by the length of the stem, and the stem can be tapered on any number of sides to achieve a reduction in diameter toward the distal end. The purpose of the taper is to provide the first portion 10 with a shape that more readily enables it to subside or sink within the medullary canal. Subsidence can be further encouraged by providing a very narrow or pointy distal end 14. However, the distal end 14 need not be sharp; and in other embodiments the distal end is rounded or spherical.

The proximal end 12 of the first portion 10 can have a diameter and/or cross-sectional geometry that causes it to bind against the opening of (or within) the medullary canal of the resectioned femur to limit subsidence. The specific diameter and/or cross-sectional geometry of the first portion 10 at the proximal end 12 is determined by the bone thickness and medullary canal diameter at the face of the resection cut. However, as pressure from weight bearing is applied to the first portion 10 over time, the subsidence of the first portion can be uncontrolled. This uncontrolled subsidence can lead to a gross leg length discrepancy (LLD) or varus/valgus tilt. Also, as the first portion subsides, it applies a greater than desirable level of compression to the bone cement leading to cement failure and particle generation. Furthermore, the proximal end 12 can subside to a point within the medullary canal wherein it exerts enough outward radial pressure to fracture the proximal end of the femur.

Figure 2:
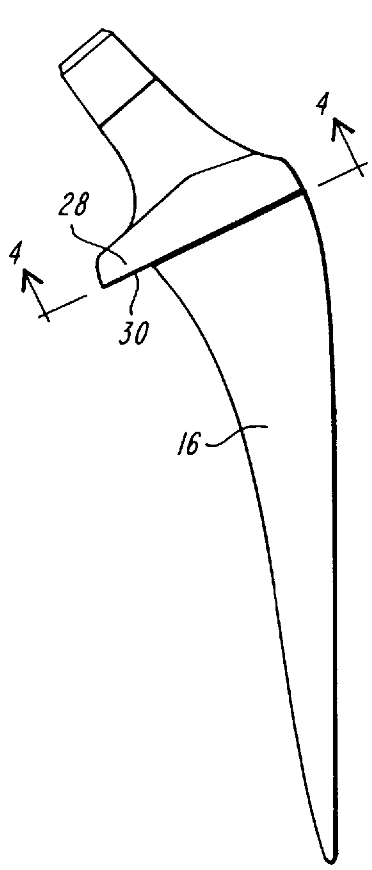
FIG. 2 is a side view of another embodiment of the invention including a collar.
Figure 3:
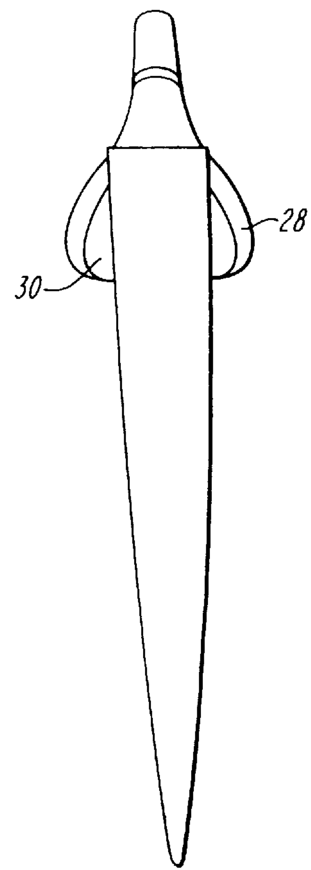
FIG. 3 is another side view of the embodiment of FIG. 2.
Figure 4:
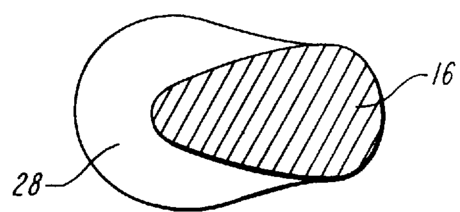
FIG. 4 is a sectional view of the embodiment of FIG. 2.

To address the above problems, other embodiments of the first portion 10 can be provided with a collar 28 at or near the proximal end 12 of the stem, as shown in FIGS. 2–4, to limit subsidence. As shown in FIGS. 2–4, the collar 28 has a diameter that is greater than the proximal end 12 of the stem. The collar 28 is also broader than the medullary canal and it includes an abutment surface 30 that engages the resectioned bone to arrest the subsidence of first portion 10. In addition to limiting downward movement of the first portion 10, the collar 28 and abutment surface 30 provide a cap that seals the end of the medullary canal to prevent bone cement particles from escaping or body fluids from infiltrating the medullary canal. The collar 28 can be configured so that it substantially matches the contour of the femoral perimeter. However, the collar 28 can be larger or smaller in diameter than the local femoral cut section.

In addition to, or instead of providing the first portion with a taper, all or a portion of the surface, or surface region, of the first portion 10 can be provided with a coefficient of friction less than 0.3 with respect to bone cement. This very slippery or lubricous coating or surface region prevents and/or significantly reduces adherence of bone cement to the stem. As shown in FIG. 1, most of the intermediate portion 16 of the stem and the distal end 14 of the stem can include a surface region 31 that has a very low coefficient of friction.

The low coefficient of friction can be achieved by providing the surface with an extremely fine finish or polish using techniques known to those skilled in the metallurgical arts. In other embodiments, the surface region includes metal that has been bombarded with an ion beam or deposit assisted by an ion beam. Examples include direct nitrogen ion implantation or sputter deposition of polyethylene utilizing an ion beam. In yet another embodiment, the surface region includes a coating of a lubricous material. Exemplary lubricous materials include calcium stearate and stearic acid. Still another embodiment includes a sheath or coating consisting of a slippery polymer or wax such as polyethylene glycol. Alternatively, the surface region can be provided with a liquid film. Exemplary liquids include sesame oil, cottonseed oil, and glycerine.

At the point of manufacture, many coating techniques are possible such as solvation, vapor deposition, ion sputtering, spraying, and electrostatic deposition. On-site application of low friction materials can include dipping, painting, wiping, and spraying. The thickness of the coating or low friction surface region can range from a few microns to a few millimeters, and is determined in large part by the material and application technique selected. For the purpose of illustration, the coating in FIG. 1 is depicted in an exaggerated manner.

Figure 5:
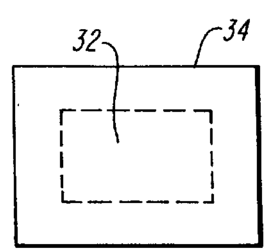
FIG. 5 is an illustration of a fluid dispenser for a joint kit in accordance with the invention.
Figure 6:
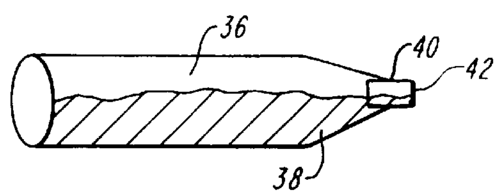
FIG. 6 is an illustration of an alternative fluid dispenser for a joint kit in accordance with the invention.

To ensure that performance parameters are achieved, an orthopedic joint kit can be provided that includes a femoral component; an acetabular cup; a bone cement; a low viscosity liquid; and a liquid dispenser for applying the liquid to the femoral component at the time of surgery. Matching the bone cement with the low viscosity liquid ensures that a stem/cement interface having a desired coefficient of friction is obtained. In an exemplary kit, the cement is polymethymethacrylate, the liquid is sesame oil or calcium stearate in a carrier solution such as mineral or vegetable oil, and the dispenser is a sterile presoaked towelette or sponge 32 which is sealed within a sterile package 34, as shown in FIG. 5. In another embodiment, shown in FIG. 6, a reservoir 36, filled with a low viscosity liquid 38, includes an outlet 40 that is filled or covered with a fluid permeable material 42.

FIG. 7 illustrates a femoral stem in accordance with the invention that is shown implanted within a resectioned femur. It should be noted that the stem is substantially or entirely enveloped with bone cement 44. Although the collar 28 is shown in an abutting relationship with the proximal end of a bone 46, this is a representation of the implant and bone after the implant has subsided. Initially, at the time of implantation, there is a small gap between the collar 28 and the bone 46. However, as weight is borne by the implant, the combination of the low coefficient of friction surface in association with the tapered stem geometry allows the stem to readily subside without pulling a cement column down as would happen with a matte finished stem. As the stem subsides, it applies a compressive force to the cement which improves load transfer at the cement bone interface. However, the collar 28 prevents excessive subsidence and overpressure on the bone cement. Once the stem has stabilized, further stem movement is limited to micromotions.

Although the invention has been shown and described with respect to exemplary embodiments thereof various other changes, omissions, and additions in forming a detail thereof may be made therein without departing from the spirit and scope of the invention.

What is claimed is:

1. A kit for an implantable orthopedic prosthesis, comprising:

a femoral component including a stem portion and a head portion;

an acetabular cup able to articulate with the head portion of the femoral component;

a bone cement for surrounding at least a portion of the stem portion of the femoral component within a medullary canal of a patient;

a low viscosity liquid for coating a portion of the stem portion of the femoral component and for reducing the coefficient of friction between the stem portion and the bone cement, wherein bonding of the bone cement and coated portion of the stem portion is substantially prevented; and a dispenser for applying the low viscosity liquid to the femoral stem.

2. The kit of claim 1, wherein the dispenser includes an absorbent material soaked with the low viscosity liquid and sealed in a sterile container.

3. The kit of claim 1, wherein the dispenser includes a reservoir for the low viscosity liquid, the reservoir having an outlet covered with a fluid permeable material.

* * * * *